United States Patent
Mauro et al.

(10) Patent No.: US 6,372,182 B1
(45) Date of Patent: Apr. 16, 2002

(54) INTEGRATED BODY FLUID COLLECTION AND ANALYSIS DEVICE WITH SAMPLE TRANSFER COMPONENT

(75) Inventors: Stephen F. Mauro, Tucson, AZ (US); Robert A. Reynolds, Escondido, CA (US)

(73) Assignee: Aalto Scientific LTD, Carlsbad, CA (US)

( * ) Notice: Subject to any disclaimer, the term of this patent is extended or adjusted under 35 U.S.C. 154(b) by 0 days.

(21) Appl. No.: 09/461,989

(22) Filed: Dec. 15, 1999

Related U.S. Application Data

(63) Continuation-in-part of application No. 09/071,630, filed on May 1, 1998, now abandoned.

(51) Int. Cl.⁷ .................................................. G01N 1/10
(52) U.S. Cl. ......................... 422/56; 422/58; 422/102; 600/584; 604/318; 604/409
(58) Field of Search .............. 422/55, 56, 57, 422/58, 61, 100, 102; 604/318, 408, 409; 600/584

(56) References Cited

U.S. PATENT DOCUMENTS

| | | | |
|---|---|---|---|
| 2,661,743 A | 12/1953 | Archer | |
| 4,008,717 A | 2/1977 | Kowarski | |
| 4,127,111 A | 11/1978 | Drolet | |
| 4,423,641 A | 1/1984 | Levy | |
| 4,444,193 A | 4/1984 | Fogt et al. | |
| 4,658,655 A | 4/1987 | Kanno | |
| 4,796,644 A | 1/1989 | Polaschegg | |
| 4,846,005 A | 7/1989 | Bacehowski et al. | |
| 4,900,321 A | 2/1990 | Kaufman et al. | |
| 5,023,055 A * | 6/1991 | Heckmann | 422/83 |
| 5,368,583 A | 11/1994 | Fleury | |
| 5,405,510 A | 4/1995 | Betts et al. | |
| 5,577,499 A | 11/1996 | Teves | |
| 5,595,187 A | 1/1997 | Davis | |
| 5,695,653 A | 12/1997 | Gsell et al. | |
| 5,758,643 A | 6/1998 | Wong et al. | |
| 5,800,781 A * | 9/1998 | Gavin et al. | 422/73 |
| 6,010,866 A * | 1/2000 | Ollington et al. | 435/7.4 |

FOREIGN PATENT DOCUMENTS

| | | |
|---|---|---|
| EP | 01 112 166 A2 | 6/1984 |
| EP | 0 317 815 A2 | 5/1989 |
| EP | 0 389 719 A2 | 10/1990 |
| EP | 0 496 515 A1 | 2/1992 |

* cited by examiner

*Primary Examiner*—Jeffrey Snay
(74) *Attorney, Agent, or Firm*—Brown, Martin, Haller & McClain

(57) ABSTRACT

A single, integrated device in which a body fluid (e.g., blood) of a human or animal can be both collected and analyzed easily and without risk of contamination is disclosed. The collection portion and analysis portion of the device are permanently joined to permit movement of small quantities of body fluid under controlled conditions, to minimize any waste of the body fluid, to ensure that no contamination reaches the main body fluid volume, and to create a permanent physical record of the results of the analysis in association with the fluid sample itself: A wide variety of different body fluid components which may be indicative of various diseases, dysfunctions and abnormalities of the human or animal or the body fluid itself can be tested for. The device includes a container for collecting human or animal body fluid, one or more testing chambers containing one or more analysis units activated by body fluid; a transfer pump or vacuum assembly to transfer one or more samples into the analysis units; and one-way valves or the equivalent to prevent any portion of the withdrawn sample from being returned to the collection container. The body fluid acted upon may be blood, blood plasma, urine, bile, pleural fluid, ascites fluid, stomach or intestine fluid, colostrom, milk or lymph.

21 Claims, 2 Drawing Sheets

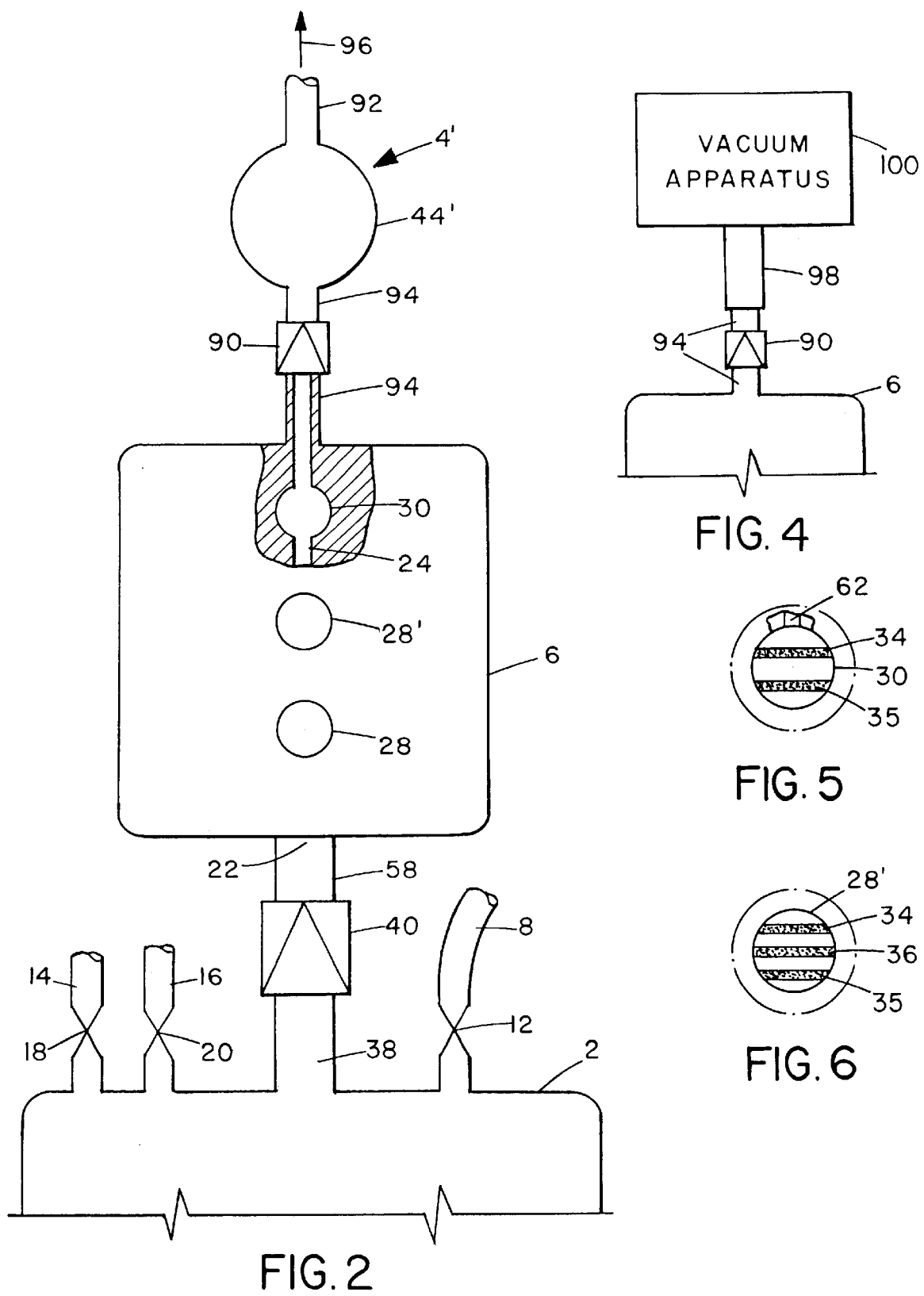

INTEGRATED BODY FLUID COLLECTION AND ANALYSIS DEVICE WITH SAMPLE TRANSFER COMPONENT

CROSS-REFERENCE TO RELATED APPLICATION

This application is a continuation-in-part of application Ser. No. 09/071,630, filed May 1, 1998, of like title, now abandoned.

BACKGROUND OF THE INVENTION

1. Field of the Invention

The invention herein relates to the collection and analysis of body fluid samples, especially blood samples, from humans or animals. More particularly it is related to devices used for such collection and analysis.

2. Description of the Prior Art

The health care industry relies on the donation of blood and plasma by many thousands of people each year. For each blood donor, a health care professional performs a venipuncture and drains a pint (or half-liter) of blood through a length of transfer tubing and into a flexible plastic bag. Plasma typically is collected into a bottle, with red blood cells being returned to the donor. The resulting filled bag or bottle is known as a "unit' of blood or plasma, After collection, each unit of blood or plasma must be tested for several infectious organisms, including the human immunodeficiency virus (HIV) and several types of hepatitis. Other tests may be performed as well. To perform these tests, a sample must be removed from each unit of collected blood or plasma. Each sample is then labeled, to identify the unit from which it was drawn, and sent to a laboratory for analysis.

Many techniques and devices are available to make these analyses. The particular ones used may vary with the substances of concern to the blood bank operator, the researcher, or whichever other party intends to use the product. Blood analyzers may range from small "per drop" analysis devices to large laboratory equipment capable of rapidly analyzing a large number of samples.

If the laboratory tests performed detect the presence of an infectious disease or other contaminant in the sample, the unit from which the sample was drawn must be identified and discarded. Personnel at the blood storage facility are responsible for matching the tested samples with their original units and correctly selecting the tainted units for disposal.

Clearly, this procedure requires considerable care and attention from everyone in the system—those who draw and label the samples, those Who issue the test results, and especially those who match the test results to the original units.

Unfortunately, although the system functions smoothly most of the time in the United States, on occasion a tainted unit of blood still finds its way into the blood pool and, eventually, into a patient who leaves the hospital with an incurable disease that he did not have when he entered the hospital. It should be mentioned that many Third World countries have too few resources to perform any screening tests at all on blood or plasma before delivering it to the end user. Consequently, although even the small degree of error encountered in the American system is unacceptable, the amount of risk incurred in other areas of the world may be staggering.

The same process—with the same risks—applies to veterinary blood supplies as well. The result of this potential for infected or contaminated blood products to be unknowingly administered to previously uninfected recipients has created a significant—and justified—level of anxiety among members of the public and among health care professionals responsible for ordering and administering these products.

Similar problems arise in the collection and analysis of other body fluids, such as urine, lymph, bile, pleural fluid, ascites fluid, stomach and intestinal fluids, colostrom, milk, and the like. While the principal emphasis in the medical field has been upon blood and blood plasma collection, because of the vast quantities collected, provision of secure collection and analysis means for other body fluids is also important and of significant interest.

Secure collection must also be followed by protection of the sample against subsequent contamination, either by handling or by the analysis testing itself. Even such acts as exposure of the sample to ambient air can introduce contaminants into the sample.

Further, whether with blood or other body fluids, it is important to have a long term record available of the properties of each sample obtained. Usually this is done for the most part by the keeping of written sample analysis records. However, written records can be misplaced or destroyed, or, most importantly, can be recognized or suspected of being incorrect. It would therefore be advantageous to have an analysis and collection/containment device which would maintain a drawn body fluid sample and its analyses in essentially permanent physical form, so that the sample and its analyses can be visually checked at a later date if written records are absent or of doubtful accuracy.

There have been devices described as useful for analysis of blood and related bodily fluids and which incorporate a test device in some manner with a collection bag or vial. See, for instance, U.S. Pat. Nos. 4,820,297; 4,846,005; 4,900,321 and 5,595,187. Such devices have not proved successful or workable for many types of blood or fluid analysis, however, since they lack features such as maintenance of permanent unaltered samples of the blood or other fluid, they do not provide for controls to confirm that the device is operating properly, or they permit contact of the sample with the ambient atmosphere or other source of contaminants.

SUMMARY OF THE INVENTION

We have now developed a single, integrated device in which a body fluid (e.g., blood) can be both collected and analyzed easily without risk of contamination. The transfer of the body fluid between the collection portion and analysis portion of the device is through a unique structure designed to permit movement of small quantities of body fluid under controlled conditions, to minimize any waste of the body fluid and to ensure that no contamination reaches the main fluid volume. The device also is permanently associated with the collection container and retains a significant quantity of the blood or other fluid in a contamination- or reaction-free condition, so that tests can be repeated at subsequent periods with consistent and reliable results. Further, control means are incorporated into the device to provide assurance the when in operation the device contains a sufficient quantity of the fluid for accurate analysis, and that the testing reagents in the device are operating accurately.

A wide variety of different body fluid components which may be indicative of various diseases, dysfunctions and abnormalities of the patient or the body fluid itself can be analyzed. In some embodiments the device is entirely hand manipulated such that the device can be used in any location, even where no external sources of power or other mechanical or electrical aids are available. In other embodiments the operation of the device can be with mechanical or electrical pumping components. The device is thus ideal for use in the field for emergency and preliminary analysis of a patient's condition, thus allowing field medical personnel to deal with such conditions as appropriate long before the patient can be transferred to more extensive medical facilities, as well as in regular blood banks and research laboratories where analysis can be substantially automated.

The device is also useful for veterinary purposes. By appropriate selection of the testing and analysis sensors to be used, body fluid drawn from animals can be rapidly analyzed, such that, for instance, a diseased animal in a herd can be quickly identified and isolated from the other animals to prevent the spread of infection within the herd. The ability to use the device in the field is of significant advantage in veterinary use, since in many cases the animals are in remote locations far from veterinary medical facilities, or it is difficult or impractical to transport the animals to such facilities.

Of particular significance with the present device is that its structure and operation ensure that the main portion of the body fluid unit drawn from the patient or donor remains isolated within the collection container during transfer of the test sample and cannot be contaminated by external contaminants, by backflow of the test sample, by transfer of testing chemicals, by contamination from improper handling of the test sample or incorrect operation of the analysis equipment, or by malfunction of the transfer or analysis equipment.

Further, because the collection container and the analysis device are permanently joined, the fluid sample and its analyses remain physically available well into the future, such that if any question subsequently arises about the properties of the sample or the analyses observed, which question cannot be answered unequivocally by the written records, the sample and the analysis units can be physically inspected and the original results verified.

The permanent combination of the collection/retention container for the bodily fluid and the testing device, with prevention of return of any portion of the fluid withdrawn from the container for testing in the testing device, is a critical element in the success of this device. Other products presently available, or which have been available in the past, while providing containment or testing, have not been the equivalent of this invention. Only with the permanent, sealed, connected structure of the present device can there be assurance that the bodily fluid sample remains uncontaminated from any source, including airborne materials, and that the test results always remain directly and permanently with the sample and its container. It is imperative in medical testing, such as blood testing, that tests of a fluid sample remain available for retesting or for confirmation of prior results, and that there be no possibility that test results for a particular sample be misfiled, misidentified or mistaken for results of a different sample. While prior art systems which involve separate of sample and test results, i.e., those in which the testing device is removable from the container, purport to be reliable in maintaining absolute identification between the sample and the test results, errors by laboratory personnel are not uncommon, labels on separated containers and test kits can come off or be rendered illegible, and many other events can occur which makes it difficult or impossible to match a bodily fluid sample and its test results once they have been separated. Such occurrences are impossible with the present invention, since the sample in its container and the test results in the testing unit are permanently joined and cannot be separated. Consequently the laboratory, the patient, the physician, and all others involved with patient care or treatment can be assured that future reference to the bodily fluid sample will find the sample uncontaminated for inspection or if further sample withdrawals are required and the original test results unequivocally associated with the sample.

Thus, not only does the present device provide a fast, easy and economical way of collecting and analyzing blood on a unit by unit basis, but it also ensures that the analysis itself, including the transfer of test sample to the analyzer, does not put the main body of the fluid unit at risk.

Therefore, the device of the present invention will be seen to be an integrated assembly that contains a bag, bottle, or other container for collecting human or animal body fluid, especially blood or plasma; one or more testing chambers containing one or more analysis units activated by the body fluid; a manual or automated pump or vacuum assembly to transfer one or more samples into one or more analysis units; and one-way valves or the equivalent to prevent any portion of the withdrawn sample from being returned to the volume of body fluid in the collection container. In one embodiment there is a pump or vacuum assembly between the main collection container and the testing chamber(s). Means are also present to insure that the device is properly filled with fluid and that the fluid is being analyzed correctly. In another embodiment the testing chamber(s) lies between the main collection container and a pump or vacuum assembly.

Thus, in a broad embodiment, the invention is of a body fluid collection and analysis device for analysis of a body fluid comprising a body fluid reservoir; a body fluid-activated analysis unit permanently associated therewith; a fluid conduit between the reservoir and the analysis unit for passage of the body fluid from the reservoir to the analysis unit; transfer means for transferring the body fluid from the reservoir to the analysis unit through the fluid conduit; and a backflow restrictor in the fluid conduit; such that no portion of body fluid transferred by the pump from the reservoir to the analysis unit returns to the reservoir.

The body fluid acted upon may be, but is not limited to, blood, blood plasma, urine, bile, pleural fluid, ascites fluid, stomach or intestine fluid, colostrom, milk or lymph.

The transfer means may be a mechanical or electromechanical pump or a vacuum fluid drawing assembly.

The analysis unit may contain a single detector for detecting the presence or absence of a single component of the body fluid which may be indicative of various diseases, dysfunctions and abnormalities of the patient or the body fluid itself. Alternatively, there may be a plurality of such detectors, each of which is configured with appropriate reactants to detect and indicate the presence or absences of different respective components of the body fluid which may be indicative of various diseases, dysfunctions and abnormalities of the patient or the body fluid itself.

Other embodiments will be described expressly below or will be evident from the descriptions below.

BRIEF DESCRIPTION OF THE DRAWINGS

FIG. 2 is a schematic representation, partially cut away or in section, of an alternative embodiment of a device of the present invention.

FIG. 4 is a schematic representation of a vacuum fluid drawing apparatus for use in the present invention.

FIG. 5 illustrates an alternative embodiment of the portion of the device designated by the circle V in FIG. 1.

FIG. 6 illustrates an alternative embodiment of the portion of the device designated by the circle VI in FIG. 1.

DETAILED DESCRIPTION AND PREFERRED EMBODIMENTS

Figures 1, 3:
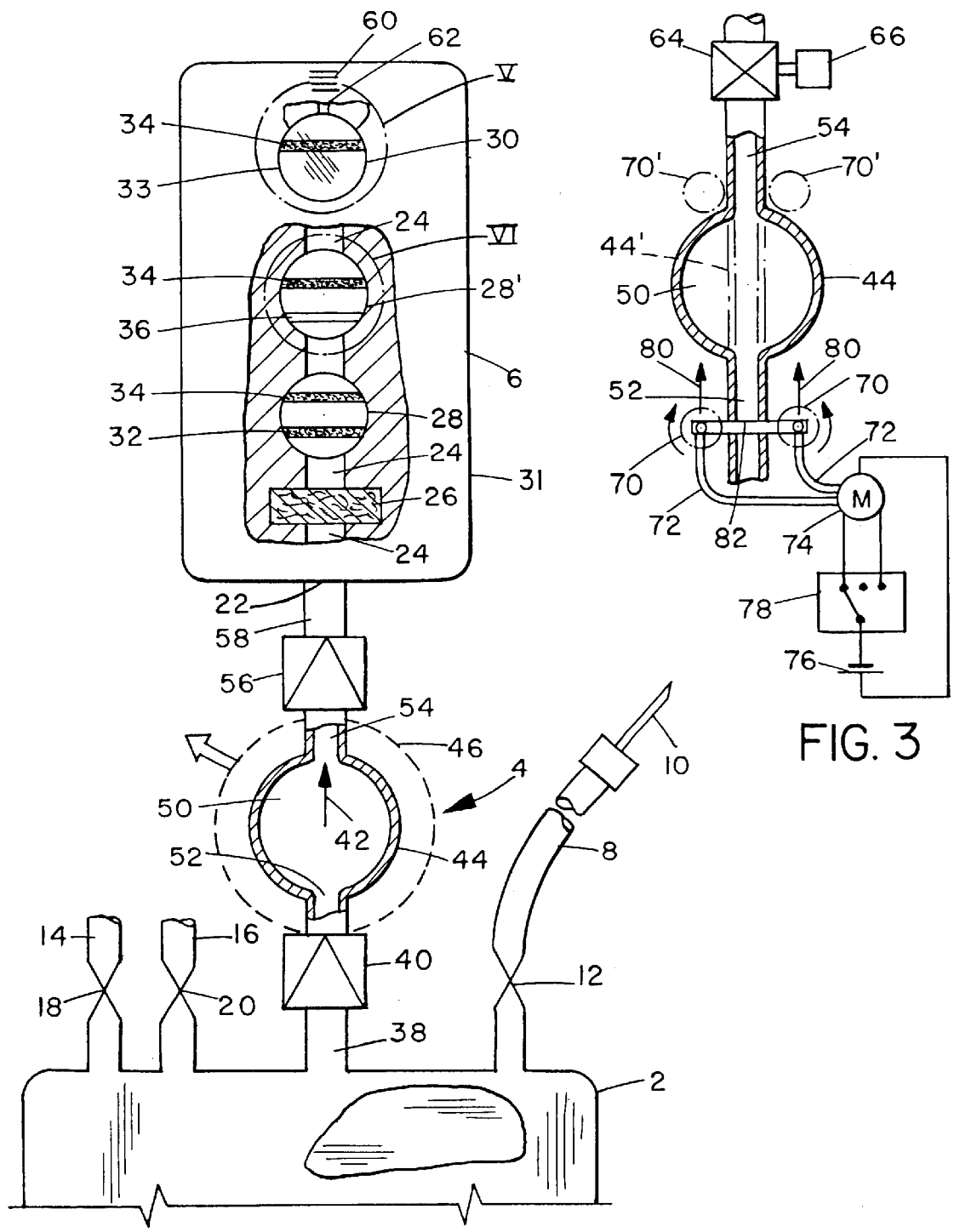
FIG. 1 is a schematic representation, partially cut away or in section, of one embodiment of a device of the present invention.
FIG. 3 is a schematic representation, also partially in section, of a representative pump useful in the present invention.

The device of the present invention is best understood by reference to the FIGS., considering first FIG. 1. For brevity herein the body fluid will be exemplified by blood. It will be understood, of course, that the same disclosure and principles apply to the collection and analysis of various body fluids, including but not limited to blood, blood plasma, urine, bile, pleural fluid, ascites fluid, stomach or intestine fluid, colostrom, milk, lymph and the like.

The body fluid (e.g., blood) collection pouch 2 portion of the device is generally similar to present blood collection pouches widely used in blood banks, hospitals, etc. It is preferably made from a flexible, transparent or translucent polymeric material, so that the bag can be easily manipulated and the amount of blood present in the pouch 2 can be readily determined by visual inspection at any time, particularly during collection. Commonly various information is written, printed or written on the outside surface of the pouch, or on labels are attached to the pouch for identification, special handling instructions, and so forth. The structure and operation of pouch 2, except to the extent that it is integrated with transfer unit 4 and analysis unit 6 in the device of the present invention, is otherwise conventional. It will also be understood that other types of containers may be used in place of pouch 2, depending on the type of body fluid to be collected, the facilities available for storage of the containers, the manner in which the containers will be handled, etc. For instance, urine is normally collected in sealable vials rather than in pouches. The type of container will be a matter of choice with the person collecting the fluid.

Considering the exemplary blood collection pouch 2, it is initially subjected to reduced pressure (partial vacuum) conditions to remove substantially all of the air initially present within the pouch. Thereafter in use it is filled with the donor's blood sample through filling tube 8 which terminates in a blood collection needle 10 which is inserted into the donor's vein. A clamp or constriction indicated at 12 is used to control the flow of the donor's blood into the pouch 2 and to close off the tube 8 when the predetermined quantity of blood has been collected. The combination of the donor's blood pressure and the partial vacuum within the pouch causes the donor's blood sample to be rapidly withdrawn and passed into the pouch 2. Other tubes 14 and 16 are commonly also molded into the pouch and provide outlets for removal of the blood for other purposes or inlets for adding materials such as preservatives or anticoagulants to the main body 11 of the unit of blood. Constrictions or clamps indicated at 18 and 20 are used to seal these tubes 14 and 16, respectively, in a conventional manner.

The blood analysis unit 6 may be any of a wide variety of flow-through analysis devices which have been used for separate analysis of blood in laboratories and hospitals for many different purposes. Blood, of course, contains many natural components such as red and white cells, platelets, hemoglobin and so forth, all of which have been extensively studied and documented. Blood composition can also be indicative of the health of the donor, particularly being indicative of the presence of disease, organ dysfunction, potentially harmful medical conditions, etc. The presence or absence of various types of antibodies, sugars, microorganisms, viruses and many other materials in a blood sample can confirm or suggest the presence in the donor of diseases such as diabetes, HIV infection, AIDS or the different types of hepatitis, or can indicate dysfunctions of organs such as the liver, heart, kidneys, and so forth. Individual detection devices to analyze for these different conditions are commercially available, and in many cases the analysis devices have been designed to simultaneously analyze for two or more conditions.

Such analyzers commonly function by having at one end a small inlet port for a sample of a particular bodily fluid (in this case, blood) from which a carrier causes the blood sample to migrate along a fluid flow path from one end of the device to the other. Along the flow path will be the analyzers; if there is more than one they will normally be in series. At the opposite (distal) end of the device is a control sensor which confirms that the blood sample has been dispersed thoroughly and completely along the entire length of the detection device and therefore has adequate sample has reached each of the intermediate analyzers, each of which is specific for a disease, dysfunction or abnormality for which the blood is being tested.

Analysis unit 6 is generally equivalent to those stand-alone devices. The blood sample is transferred to the inlet 22 at the proximal end of the analyzer 6 by the pumping unit 4 in the manner to be described below. The blood sample flows into and fills flow path 24. Upon entry into the analysis unit 6 the blood sample first encounters filter 26 which removes solid components, notably cellular material. The specific types and sizes of solids to be removed will be determined by the pore size of the filter 26. The blood filtrate flows on through a continuation of flow path 24 to a single analysis unit 28 or, usually, through a plurality of such units joined by segments of flow path 24. There may be any convenient number of such units in the plurality; in the embodiment exemplified in FIG. 1, two analysis units are shown and designated respectively 28 and 28'. After passing through the last of the units 28, 28', . . . , the blood filtrate passes through the final segment of flow path 24 to control sensor 30.

Each of the units 28, 28'. . . is normally used to analyze for an indicator of a different target disease, dysfunction or abnormality, which will be predetermined by the specific purpose of the blood analysis. For instance, one analysis unit 28 may have chemical, monoclonal or other constituents to detect the presence of antibodies to the HIV virus, while the next unit 28' may be intended to detect the presence of one or more of the various strains of hepatitis. Conversely, two or more, or all, of the analysis units 28, 28', . . . , may be chosen to test for the same disease, either to confirm one another or to provide multiple detection protocols for the target disease. Similarly, a sensor may be designed to detect the absence of a component that would ordinarily be in the blood stream and thereby identify a donor's condition for a disease, dysfunction or abnormality which is indicated by the absence of a specific component.

The presence or absence of the predetermined component in each of the sensors may be indicated in a variety of different ways, most of which involve the use of a visual indicator which appears or fails to appear during the analysis. The embodiment of FIG. 1 shows a typical example of such indication. The housing 31 of the analysis unit 6 is formed of an opaque plastic, metal, etc. with a series of holes 33 in it, each hole 33 aligned with an analysis or control unit 28, 28', . . . , 30 so that the face of the unit can be observed.

In turn, each face of a unit 28, 28', ..., 30 is transparent, or is a transparent portion of the analysis or control unit's own housing. Thus the operator can observe the condition of the pretreated substrate within the analysis or control unit. Each unit's substrate is commonly treated with a detection chemical, monoclonal antibody, etc., preferably in a distinctive shape or pattern. Typically before the test the treated area is clear or of a specific "unreacted" color. When the blood fluid flows through the unit, if the component to be detected is not present, there is no reaction with the treating chemical, and the treated area remains clear without appearance of the pattern, or stays the original "unreacted" color. On the other hand, if the blood does contain the desired component, a reaction between that component and the detecting substance occurs. The color of the treated area changes substantially and/or the distinctive pattern appears on the substrate, both the new color and the pattern being visible through the transparent portion of the sensor. Commonly, the treated portions are printed in the pattern of a wide line, a circle, a cross, etc. Whether the color change or pattern appearance represents a positive or negative result, of course, depends on what is being tested for. If one is seeking the presence of a blood component, the color change or pattern appearance is positive, whereas if the absence of the component is sought, the same change represents a negative result. Conversely, lack of a change is positive if absence of the component is sought and negative if its presence is sought.

For example, in FIG. 1, sensor 28 shows a typical pattern with a positive result for a component whose presence is sought to be detected. The analysis unit 28 has two horizontal bands impregnated with detection chemicals, the first band 32 being the band to detect the desired blood component and the second band 34 being a control band, which will be described below (and which is present in each analysis and control unit). In the case of the illustrated unit 28, a positive result has occurred and the band 32 has become a dark color (or visible, if it were initially clear) as indicated by the shading, thus indicating that the blood does contain the sought after component. On the other hand, in unit 28', the test strip 36 remains clear or of a light color, indicating that a second sought after component is not present in the blood. Finally, at the opposite end of the analyzer 6 from the entry port 22 is control unit 30, which contains only the single control band 34.

The purpose of band 34 in each unit 28, 28', ..., 30 is to insure that the blood has reached, passed through and saturated all of the various units. The use of control unit 30 at the end of flow path 24 is to confirm that the blood fluid has passed through the entire analysis unit 6. The confirmation chemical or monoclonal antibody in band 34 can be chosen so that the condition of the blood at each unit can be determined, to insure that a significantly strong concentration of the blood has reached each of the units. Most conveniently this is accomplished by making the degree of color change occurring in band 34 dependent on the condition of the blood. Of course, where the condition of the blood as it passes through the analysis unit is either not significant or is expected to be substantially unchanged, the function of the control sensor 30 will merely be to confirm that at least some of the blood has traversed the entire length of the unit 6 and the detection chemical will be selected accordingly.

Similarly, it is desirable to have a second control band 35 which insures that the reaction at test strip 36 can be expected to be accurate, as illustrated in FIGS. 5 and 6. Control band 35 contains a reactant for which the reaction with the blood or bodily fluid is known to be positive both qualitatively and quantitatively. The expected position reaction at each band 35 therefore indicates that the fluid in that unit 28, 28', 30, ..., is the fluid that it is supposed to be, and is present in the intended concentration and composition. Since control band 35 thus confirms to the user of the device that the known reaction has occurred in the manner expected, the user can then be confident that the reaction of the test strip 36 has a high probability of being a true result.

It will also be appreciated that for some fluids and reactions, the functions of bands 34 and 35 can be combined into a single dual-purpose reactant, whose reaction indicates both the proper filling of each test unit 28, 28', 30, ..., and the accuracy of the test result.

The various analysis units 28, 28', ..., may, as indicated, be intended to detect different diseases or conditions or some or all of the sensors may be intended to detect the same condition either by using different detection means as a cross check, or by repeating the same detection to ensure that a single detector did not give a false reading.

The mechanism for transferring the blood sample from the blood collection pouch 2 to the analysis unit 6, the transfer mechanism 4, is critical to the present invention. It is this transfer unit 4 which allows a precise amount of the blood sample to be withdrawn from the pouch 2 and transferred to the analysis unit 6 without loss or contamination of the main body 11 of the blood, which remains in pouch 2, and which ensures that the blood sample will be forced throughout the analysis unit 6. In the embodiment shown in FIG. 1, the transfer unit 4 is connected to the pouch 2 by conduit 38 which terminates in one-way valve 40. Valve 40 allows blood to flow only "downstream," i.e., in the direction from the pouch to the analyzer 6 as indicated by arrow 42. No backflow or "upstream" flow of blood is permitted through valve 40, thus ensuring that no blood which is extracted from pouch 2 is allowed to return, thus ensuring that no contamination which might occur to the blood sample after withdrawal will be imparted to the main body 11 of the blood in pouch 2.

Attached on the downstream side of valve 40, opposite the conduit 38, is pump 44. Pump 44 in the embodiment illustrated in FIG. 1 is in the form of an expanded conduit which encloses a chamber 50 with an inlet 52 which is connected to the outlet of valve 40. The walls of the pump 44 are made of a flexible thermoplastic or elastomeric material, such as a natural or synthetic rubber, polyethylene, polypropylene, polytetrafluoroethylene (PTFE) or other well known material used for making medically acceptable tubing and similar conduits. Preferably the material comprising the walls of pump 44 will be transparent or translucent so that the quantity of blood which is in chamber 50 will be visually evident.

At the other end of chamber 50 of pump 44 is outlet 54 which connects with the inlet of a second one-way valve 56. Valve 56 is oriented in the same downstream flow direction as valve 40 and serves to ensure that any blood which is pumped out of pump 44 into analysis unit 6 does not flow back into pump 44. The outlet of valve 56 and the inlet port 22 of analysis unit 6 are connected by conduit 58.

It is critical that the collection container 2 and the analysis unit 6 be permanently connected, either through transfer unit 4 as in the embodiment of FIG. 1, or directly through a conduit 38/58 as in the embodiment of FIG. 2. Only by maintaining the container 2 and the analysis unit 6 together permanently can the archival function of the device—i.e., the retention of the sample 11 and the results of the analyses in detectors 28, 28', ..., —be accomplished.

From this description, the operation of the entire device can be readily understood. A blood sample is taken from a donor or patient in the conventional manner using needle 10, through which the withdrawn blood is passed through conduit 8 into pouch 2. Neither the flow rate of the blood into the bag nor the volume of blood collected is sufficient to open valve 40. When the bag has been filled with the predetermined quantity of the main body 11 of the donor's blood, the tube 8 is sealed at constriction or clamp 12 and the needle 10 is withdrawn from the donor or patient. Commonly thereafter the tube 8 is permanently sealed a short distance outside constriction 8 and the remaining length of the tube 8, including the needle 10, is discarded. The body 11 of blood in the pouch 2 is now ready for analysis.

The operator then squeezes the flexible pouch 2 to force a sample of blood through one-way valve 40 and into chamber 50 of pump 44. The flow of the blood into chamber 50 is under sufficient pressure to exhaust air through one-way valve 56 and through flow path 24 of analysis unit 6, venting the air through a distal gas outlet 62 leading to vent 60 on the exterior of the housing 31 of analysis unit 6. The operator's hand pressure on the blood pouch 2 serves to fill chamber 50, but is not sufficient to force the blood sample through one-way valve 56 and into the analysis unit 6. This may be accomplished by having valve 56 being somewhat more resistant to flow than valve 40, or a flow shut-off valve 64 may be inserted into outlet conduit 54 upstream of one-way valve 56. Valve 54 may be operated by any convenient off/on device such as thumbscrew 66 (FIG. 2).

The filling of chamber 50 of pump 44 allows for relatively precise measurement of the volume of blood withdrawn from pouch 2 to be obtained. To this end, the material from which the walls of pump 44 are made will be of a material and wall thickness which provides sufficient stiffness to resist stretching or ballooning, yet not so stiff that it cannot be easily compressed when squeezed by the operator's fingers, thus providing that the full chamber 50 will have a substantially constant and known volume.

Once the chamber 50 is full of blood, the operator ceases squeezing pouch 2 and begins squeezing the walls of pump 44 to force the blood out through outlet conduit 54 and through valve 56 (valve 60 having previously been opened if present) and through conduit 58 and inlet 22 into the flow path 24 of analysis unit 6. The finger pressure on the conduit 44 will be such as to move the blood through the unit 6, but not so great as to create a flow velocity which will disrupt the filter 26 or any of the analysis or control units 28, 28', . . . , 30. Since the faces of the units 28, 28', . . . , 30 are transparent, the operator will be able to visually note the progress of the blood fluids through these sensors and will be able to control the pressure on the pump 44 accordingly. The volumetric size of the chamber 50 will be calculated originally with regard to the sizes of the analysis units 6 which are to be used within the invention, so as to minimize the amount of blood removed from the main body 11 and avoid the presence of an excessive quantity of blood in the chamber 50 as compared to what is needed to activate the analysis units, but still to have sufficient blood present to ensure that all the analysis units are completely filled with blood fluid, taking into consideration that not all of the blood in chamber 50 can be expelled by finger compression of the pump 44. The appropriate hand- and finger-pressure needed by the operator for manipulation of pouch 2 and pump 44 will be readily learned.

An alternative embodiment of the device of the invention is illustrated in FIG. 2. In this embodiment the collection container 2 and the analysis unit 6 are in direct fluid communication and permanently connected through conduits 38 and 58 and one-way valve 40, which all operate as discussed above. If desired, both valves 40 and 56 may be present in the conduit 38/58 to provide additional security against return of any blood to the container 2. Transfer means 4' in this embodiment is disposed distally of the analysis unit 6 and operates to draw the blood 11 out of the container 2 and through the analysis unit 6 by pump suction or vacuum. To accomplish this the gas outlet 62 and vent 60 are replaced by fluid conduit 94, in which is disposed one-way valve 90. When pump 44' is activated, it creates a suction in conduit 94. Since conduit 94 connects through unit 30 with conduit 24, and then on through conduits 38/58 with container 2, the suction created by pump 44' draws blood 11 from container 2 and into and through each of the units 28, 28', . . . , and 30. To insure that blood has fully traversed into and through all detectors of unit 6, it is advisable to continue operation of pump 44' until blood appears in pump outlet conduit 92 and a small amount is exhausted with the expelled air as indicated by arrow 96. The presence of one-way valve 90 then prevents air from returning to the analysis unit 6, maintaining each of the units 28, 28', . . . , and 30 full of blood. Transfer unit 4' may thereafter be disconnected from the device, leaving the collection container 2 and the analysis unit 6 attached as a unitary combination. This will be discussed further below in connection with FIG. 4.

The manual operation of the pump 44 and 44' is the preferred embodiment, since it is simple to manufacture and use, can be used anywhere and under virtually any condition, requires no outside source of power, and minimizes the size of the pump 44 or 44'. Alternatively, however, if there are to be many tests of drawn blood to be made in a large number of the devices of this invention, it may be desirable to have a mechanized way of pumping the blood from container 2 into unit 6. Such an embodiment is shown in FIG. 3 which represents an alternative embodiment of the transfer unit 4 (or equivalently for transfer unit 4'), within the dashed circle 46. In this case, a pair of motor driven rollers 70 are placed around the inlet conduit 52. These may be driven by flexible worms 72 from electric motor 74, which in turn is powered by battery 76 through center-off reversing switch 78. As the rollers move downstream as indicated by arrows 80, they gradually compress the walls of pump 44 reducing the size of chamber 50 and forcing the blood through outlet conduit 54 and on through valves 64 and 56 to unit 6 as described previously. Once the rollers reach the position 70' so that the pump 44 has been reduced in diameter to the shape shown at 44', the motor 74 is stopped. Thereafter, when it is desired to reset the unit, the reversing switch 78 is thrown and the motor reverses the direction of the rollers' travel returning them to the original position at 70. While the reversing switch preferable has the off/on control, there may alternatively be a separate off/on switch in the motor/battery circuit. In order to reuse the system for a different pouch and analysis unit, removal bar 82 is provided which links the axles of the two rollers 70. When this bar is removed, the rollers can be separated and dismounted from the conduit 52. They can then be mounted on another device surrounding that device's conduit 52 and coupled into place by replacement of the bar 82, making the motor/roller system ready for reuse.

The embodiment of FIG. 2 also lends itself to operation of the device with vacuum fluid transfer apparatus 100 as shown in FIG. 4. This apparatus may be a vacuum pump, an aspirator, or any other convenient means of creating the previously suction in conduit 94. The vacuum apparatus 100 may be connection to conduit 94 by vacuum tubing 98, and in used in place of pump 44'. It will be operated in an analogous manner to pump 44', including drawing up a slight excess of blood 11 to insure that all detectors in analysis unit 6 are completely filled with blood. Since it is contemplated that the vacuum apparatus 100 will be disconnected from the device once the unit 6 has been filled with blood, it is desirable to make conduit 94 sufficiently long that it can be sealed distally of valve 90 to insure that disconnection of the apparatus 100 and uncoupling of conduits 94 and 98 will not allow air incursion into conduit 94, notwithstanding valve 90. The same should be done when transfer unit 4' is removed from conduit 94.

The device of the present invention will find widespread use in many areas of medical treatment and analysis not limited to only the general testing of blood supplies for blood bank use and research, as described above. Other areas of use include plasmapheresis in which patients are bled frequently, but in which heretofore the blood has not been tested at the same intervals; in emergency medical cases where rapid blood typing or the identification of Rh factors is important; or in other emergency situations such as combat where there may be a need to provide immediate blood transfusions without being able to draw on the supplies of conventional blood banks. The use of the device is particularly significant in ensuring that all blood of donors and patients can be tested to prevent potentially hazardous agents in blood from being passed on from donors who are asymptomatic carriers of the infectious or other hazardous agents. It will also find extensive use in research where rapid screening is needed to go through a large number of blood samples and identify for further use only those which contain a particular agent or component. With such ability to do rapid screening directly of the blood samples, the desired samples can be readily and quickly identified, thus speeding the research and dramatically reducing the costs associated with conventional blood testing.

It will be evident to those skilled in the art that there are numerous embodiments of this invention which, while not expressly set forth above, are clearly within the scope and spirit of the invention. The above description is therefore to be considered exemplary only and the invention is to be limited solely by the appended claims.

We claim:

1. An integrated body fluid collection and analysis device for analysis of a body fluid comprising:
    a body fluid reservoir;
    a body fluid-activated analysis unit permanently associated therewith;
    a fluid conduit between said reservoir and said analysis unit for passage of said body fluid from said reservoir to said analysis unit;
    transfer means for transferring said body fluid from said reservoir to said analysis unit through said fluid conduit; and
    a backflow restrictor in said fluid conduit;
    such that no portion of body fluid transferred by said pump from said reservoir to said analysis unit returns to said reservoir.

2. A device as in claim 1 wherein said transfer means is disposed in said fluid conduit.

3. A device as in claim 2 wherein said backflow restrictor is disposed between said transfer means and said reservoir.

4. A device as in claim 2 wherein said backflow restrictor is disposed between said transfer means and said analysis unit.

5. A device as in claim 1 wherein said transfer means is disposed in fluid communication with an end of said analysis unit distal from said reservoir.

6. A device as in claim 1 wherein said transfer means is manually operated.

7. A device as in claim 6 wherein said transfer means comprises a chamber enclosed by a flexible wall and is operated by manual compression of said flexible wall when said body fluid is present in said chamber.

8. A device as in claim 1 wherein said transfer means comprises a mechanical or electromechanical pump or a vacuum fluid drawing assembly.

9. A device as in claim 1 wherein said body fluid acted upon comprises blood, blood plasma, urine, bile, stomach or intestine fluid, colostrom, milk or lymph.

10. A device as in claim 1 wherein said analysis unit comprises detection means for detecting and indicating the presence or absence in said body fluid of a component of said body fluid, said presence or absence being indicative of disease, abnormality or dysfunction of a human or animal from which said body fluid was obtained.

11. A device as in claim 10 wherein said analysis unit comprises a plurality of detection means, each said detection means of said plurality for detecting the presence or absence in said body fluid of a different component of said body fluid each indicative of disease, abnormality or dysfunction of said human or animal from which said body fluid was obtained.

12. A device as in claim 10 wherein said analysis unit further comprises a first control detector providing confirmation that said body fluid transferred by said transfer means has entirely filled said analysis unit.

13. A device as in claim 10 wherein said detection means comprises a chamber having therein a material sensitive to the presence of said component of said body fluid, activation of said material by said component in said body fluid causing by a visible change in the appearance of said material, said chamber being enclosed by a wall which comprises a viewing area though which said visible change may be observed, such that said detection means manifests identification of said presence or absence of said component by the appearance or non-appearance of said visible change within said viewing area.

14. A device as in claim 13 wherein said material is disposed within said chamber in a distinctive pattern and said visible change comprises appearance of color or change of color in said material in said pattern.

15. A device as in claim 11 wherein each said detection means in said plurality comprises a chamber having therein a material sensitive to the presence of said component of said body fluid for which said detection means is directed, activation of said material by said component in said body fluid causing by a visible change in the appearance of said material, said chamber being enclosed by a wall which comprises a viewing area though which said visible change may be observed, such that said detection means manifests identification of said presence or absence of said component by the appearance or non-appearance of said visible change within said viewing area.

16. A device as in claim 15 wherein in each said detection means said material is disposed within said chamber in a distinctive pattern and said visible change comprises appearance of color or change of color in said material in said pattern.

17. A device as in claim 12 wherein said control detector comprises a chamber having therein a material sensitive to the presence of said body fluid, activation of said material by said body fluid causing by a visible change in the appearance of said material, said chamber being enclosed by a wall which comprises a viewing area though which said visible change may be observed, such that said detection means manifests confirmation that said body fluid has reached said control detector by the appearance or non-appearance of said visible change within said viewing area.

18. A device as in claim 17 wherein said material is disposed within said chamber in a distinctive pattern and said visible change comprises appearance of color or change of color in said material in said pattern.

19. A device as in claim 10 wherein said analysis unit further comprises a second control detector comprising a reactant which reacts with said body fluid in a known manner and provides an indication confirming such known reaction, said indication providing confirmation of the nature of said bodily fluid.

20. A device as in claim 19 further comprising a first control detector providing confirmation that said body fluid transferred by said transfer means has entirely filled said analysis unit.

21. A device as in claim 20 wherein said first control detector and said second control detector comprise a single unitary control detector which provides confirming functions of both said first control detector and said second control detector.

* * * * *